(12) United States Patent
Raz et al.

(10) Patent No.: US 12,618,938 B2
(45) Date of Patent: May 5, 2026

(54) SENSING APPARATUS FOR A VEHICLE

(71) Applicant: Gentex Corporation, Zeeland, MI (US)

(72) Inventors: Guy Raz, Binyamina (IL); Robert Steel, Coventry (GB)

(73) Assignee: GENTEX CORPORATION, Zeeland, MI (US)

( * ) Notice: Subject to any disclaimer, the term of this patent is extended or adjusted under 35 U.S.C. 154(b) by 436 days.

(21) Appl. No.: 18/118,214

(22) Filed: Mar. 7, 2023

(65) Prior Publication Data

US 2023/0288529 A1 Sep. 14, 2023

Related U.S. Application Data

(60) Provisional application No. 63/318,066, filed on Mar. 9, 2022.

(51) Int. Cl.
| | |
|---|---|
| *G01S 7/02* | (2006.01) |
| *A61B 5/00* | (2006.01) |
| *A61B 5/05* | (2021.01) |
| *A61B 5/08* | (2006.01) |
| *B60J 3/04* | (2006.01) |
| *G01S 13/02* | (2006.01) |
| *H01Q 1/12* | (2006.01) |
| *H01Q 1/32* | (2006.01) |
| *H01Q 3/36* | (2006.01) |
| *H01Q 9/04* | (2006.01) |

(52) U.S. Cl.
CPC ............... *G01S 7/028* (2021.05); *A61B 5/05* (2013.01); *A61B 5/0816* (2013.01); *A61B 5/6893* (2013.01); *H01Q 1/1271* (2013.01); *H01Q 1/3233* (2013.01); *H01Q 1/325* (2013.01); *H01Q 3/36* (2013.01); *H01Q 9/0407* (2013.01); *B60J 3/04* (2013.01); *G01S 2013/0245* (2013.01)

(58) Field of Classification Search
CPC .... H01Q 1/1271; H01Q 1/325; H01Q 21/065; H01Q 1/3275; H01Q 21/30; H01Q 3/36; H01Q 1/3291; H01Q 1/38; G01S 13/931; G01S 2013/93276; G01S 2013/0245; B60R 21/0136; B60R 1/04; B60J 3/04; B60J 1/02; B60J 1/00; B60J 10/00
See application file for complete search history.

(56) References Cited

U.S. PATENT DOCUMENTS 9,753,121 B1 * 9/2017 Davis ..................... G01S 7/282
11,024,941 B2 6/2021 Funatsu
(Continued)

FOREIGN PATENT DOCUMENTS

| AU | 2017260101 A1 | 11/2018 |
|---|---|---|
| JP | 2006213206 A | 8/2006 |

(Continued)

*Primary Examiner* — Vladimir Magloire
*Assistant Examiner* — Peter Davon Doze
(74) *Attorney, Agent, or Firm* — Price Heneveld LLP; Brian James Brewer

(57) ABSTRACT

A sensing apparatus for a vehicle includes a window, a wireless sensing circuit, and a controller. The wireless sensing circuit includes a conductive coating coupled to the window. The conductive coating includes an antenna array that is configured to communicate a radio frequency at a phase angle. Further, a controller is in communication with the antenna array and configured to communicate a first signal to the antenna array to control the phase angle.

19 Claims, 6 Drawing Sheets

(56)                    References Cited

U.S. PATENT DOCUMENTS

| | | | |
|---|---|---|---|
| 2002/0140215 A1 | 10/2002 | Breed et al. | |
| 2002/0154377 A1* | 10/2002 | Pepper ..................... | G02F 1/292 |
| | | | 359/254 |
| 2005/0232469 A1* | 10/2005 | Schofield ........... | B60W 30/143 |
| | | | 382/104 |
| 2017/0274832 A1 | 9/2017 | Abe | |
| 2018/0037007 A1* | 2/2018 | Droste ................. | H01Q 9/0428 |
| 2018/0205156 A1* | 7/2018 | Li ..................... | G02F 1/133382 |
| 2019/0319335 A1* | 10/2019 | Hughes ................ | H01Q 9/0407 |
| 2021/0021959 A1* | 1/2021 | MacNeille ............ | H04N 23/57 |
| 2021/0359774 A1* | 11/2021 | Tertinek ............. | G01S 13/0209 |
| 2021/0389447 A1* | 12/2021 | Shams ................... | G01S 13/82 |

FOREIGN PATENT DOCUMENTS

| | | | | |
|---|---|---|---|---|
| JP | 2019140669 A | * 8/2019 | ............... | B60J 1/00 |
| WO | 0050261 A2 | 8/2000 | | |
| WO | 2019178282 A1 | 9/2019 | | |

* cited by examiner

SENSING APPARATUS FOR A VEHICLE

CROSS-REFERENCE TO RELATED APPLICATION

This application claims priority to and the benefit under 35 U.S.C. § 119(e) of U.S. Provisional Application No. 63/318,066, filed on Mar. 9, 2022, entitled "SENSING APPARATUS FOR A VEHICLE," the disclosure of which is hereby incorporated herein by reference in its entirety.

TECHNOLOGICAL FIELD

The present disclosure relates to a sensing apparatus for a vehicle, and more particularly to an antenna array of a sensing apparatus incorporated with a window of a vehicle.

SUMMARY OF THE DISCLOSURE

According to one aspect of the present disclosure, a sensing apparatus for a vehicle includes a window, a wireless sensing circuit, and a controller. The wireless sensing circuit includes a conductive coating coupled to the window. The conductive coating includes an antenna array that is configured to communicate a radio frequency at a phase angle. Further, a controller is in communication with the antenna array and configured to communicate a first signal to the antenna array to control the phase angle.

According to another aspect of the present disclosure, a window for a vehicle includes a first substrate including a first surface and a second surface, a second substrate including a third surface and a fourth surface, a first electrode disposed on the third surface, an electro-optic medium disposed between the first electrode and the second surface, and a plurality of patch antennas disposed adjacent to the second surface. Further, the plurality of patch antennas is substantially transparent in a visible light spectral range.

According to yet another aspect of the present disclosure, a sensing apparatus for a vehicle includes a window, a wireless sensing circuit, and a controller. The wireless sensing circuit includes a conductive coating coupled to the window. The conductive coating includes a plurality of antennas and more than one electrical conductor. Each electrical conductor is in contact with some but not all of the plurality of antennas. Further, a controller is in communication with the more than one electrical conductor and configured to communicate a first signal to some of the plurality of antennas to provide a first phase angle and a second signal to some of the plurality of antennas to provide a second phase angle.

These and other features, advantages, and objects of the present device will be further understood and appreciated by those skilled in the art upon studying the following specification, claims, and appended drawings.

Figure 1:
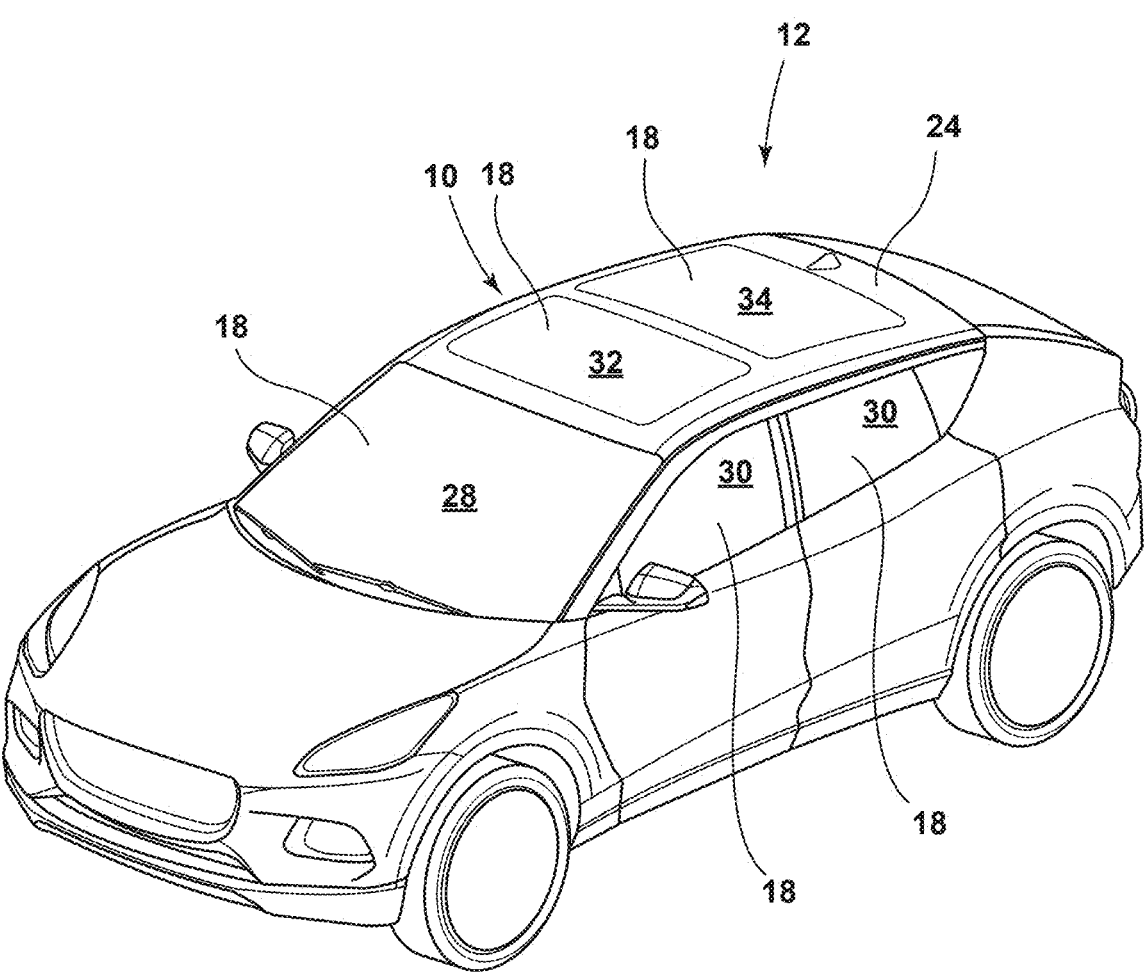
FIG. 1 is a top perspective view of a vehicle including one or more windows that incorporate a sensing apparatus according to one aspect of the disclosure.

The components in the figures are not necessarily to scale, emphasis instead being placed upon illustrating the principles described herein.

DETAILED DESCRIPTION

The present illustrated embodiments reside primarily in a combination of apparatus components related to an improved sensing apparatus for a vehicle. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

The term "about" simply accounts for expected nominal variations as a result of manufacturing and/or operational limitations and tolerances, for example, within 5% of the recited value.

Figure 4A:
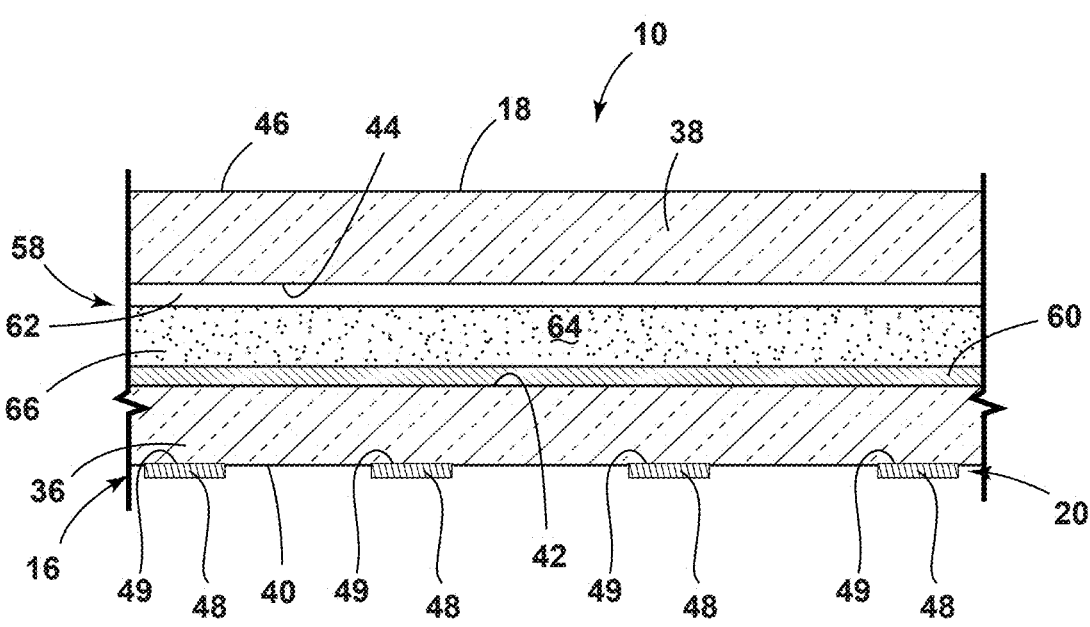
FIG. 4A is a cross-sectional view of a sensing apparatus incorporating an antenna array into an electro-optic element according to one aspect of the present disclosure.
Figure 4B:
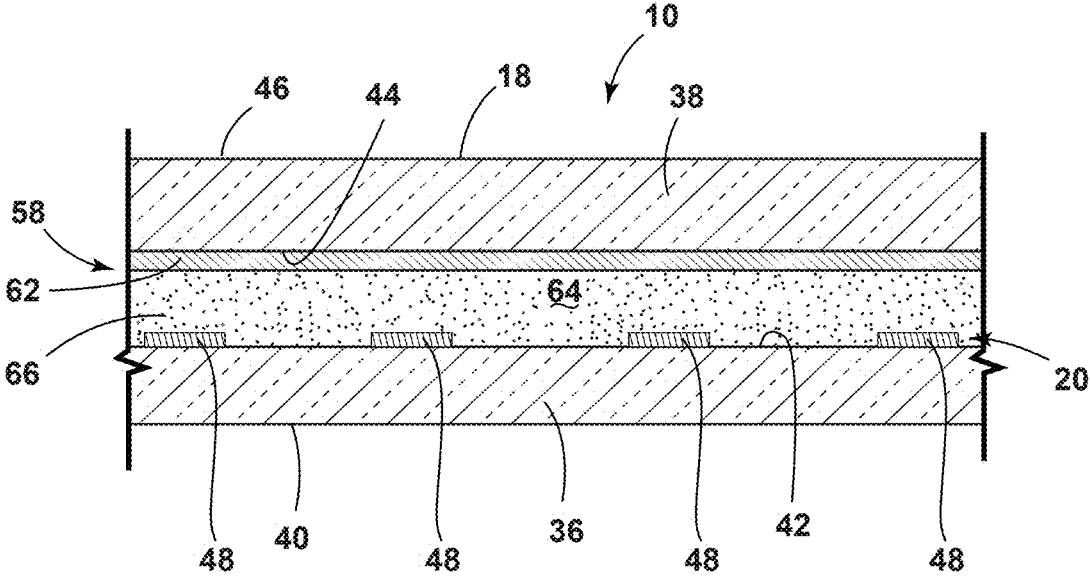
FIG. 4B is a cross-sectional view of a sensing apparatus incorporating an antenna array into an electro-optic element according to another aspect of the present disclosure.
Figure 5:
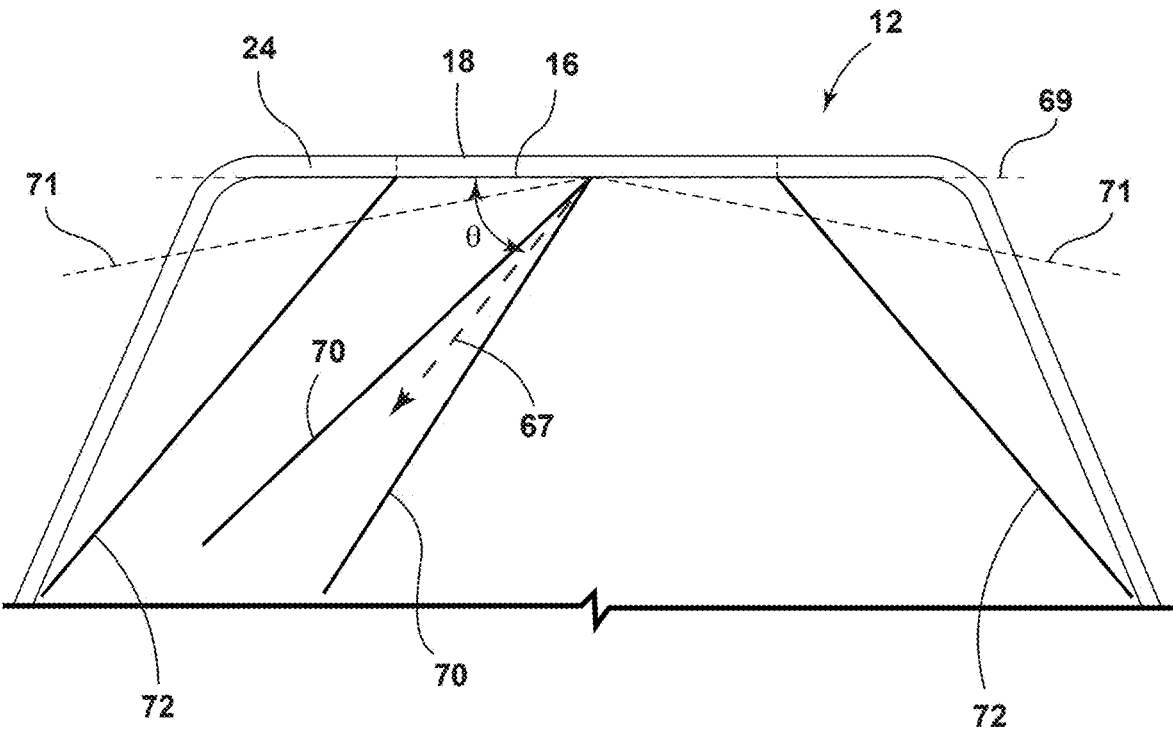
FIG. 5 is a cross-sectional view of a vehicle illustrating an exemplary phase beam of the antenna array.
Figure 6:
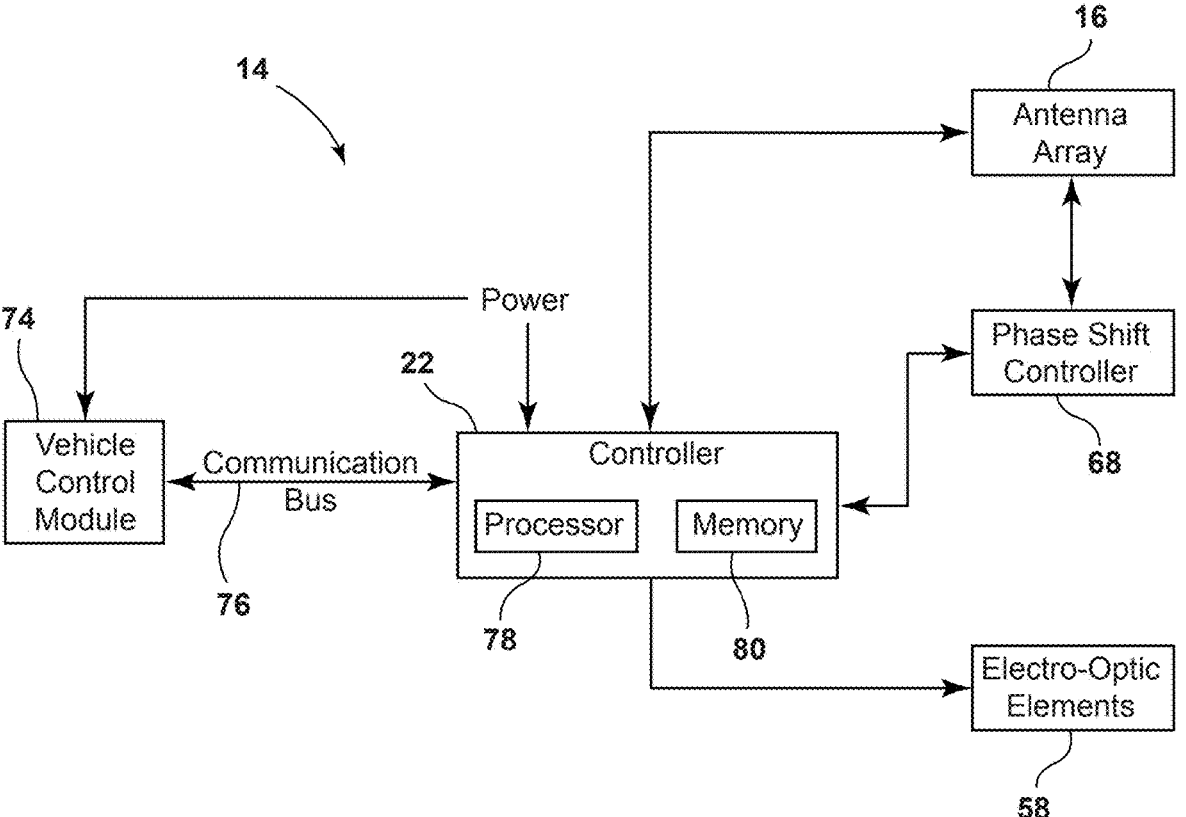
FIG. 6 is a block diagram of a wireless sensing circuit in accordance with the present disclosure.

Referring to FIGS. 1-6, a sensing apparatus 10 for a vehicle 12 includes a wireless sensing circuit 14 (FIG. 6). The sensing apparatus 10 further includes an antenna array 16 configured to communicate a radio frequency signal at a phase angle Θ (FIG. 5). The antenna array 16 may be formed on a window 18 as part of a conductive coating 20. A controller 22 is in communication with the antenna array 16 and configured to communicate a first signal to the antenna array 16 to control the phase angle Θ.

Referring to FIG. 1, the sensing apparatus 10 may be used in a vehicle 12, such as an automotive vehicle, as illustrated. While generally illustrated as incorporated with a sunroof window 18 adjacent to a vehicle roof 24, the antenna array 16 may be incorporated into any type of window 18 of a building, vehicle 12, or any other structure that may incorporate the window 18. For example, the antenna array 16 may be incorporated into the window 18 and the window 18 may be configured as a windshield 28, a side window 30, a front sunroof window 32, and/or a rear sunroof window 34 of the vehicle 12. It is generally contemplated that the placement of the antenna array 16 in the front and/or rear sunroof windows 32, 34 may allow the antenna array 16 to have a range encompassing an entire interior cabin of the vehicle 12. It should be appreciated that the antenna array 16 may also be incorporated into different types of sunroof windows other than the sunroof windows 32, 34 illustrated in FIG. 1, for example a panoramic sunroof window.

Figure 2:
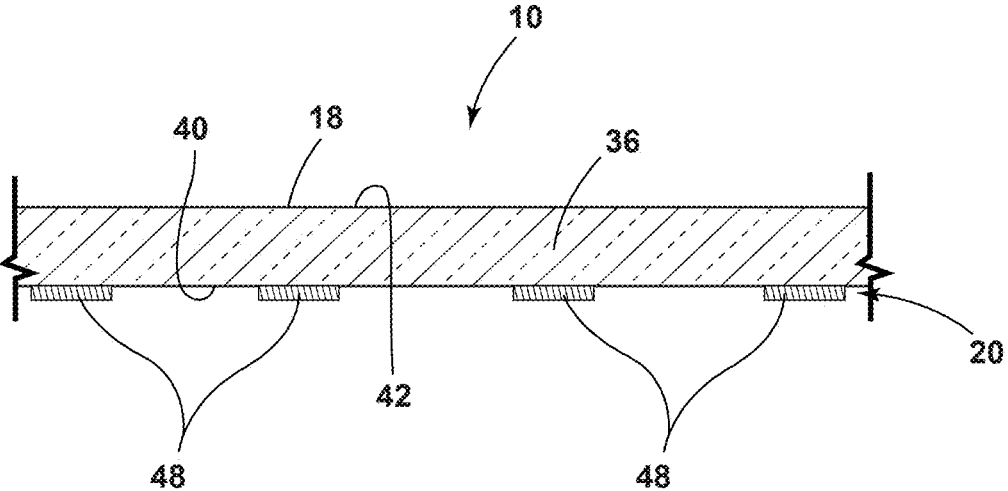
FIG. 2 is a fragmentary cross-sectional view of a sensing apparatus taken along the line II of FIG. 3.

Referring now to FIG. 2, the illustrated window 18 includes a first substantially transparent substrate 36 and may include a second substantially transparent substrate 38 (see FIGS. 4A and 4B). The first substantially transparent substrate 36 includes a first surface 40 that faces the interior cabin of the vehicle 12 and a second surface 42 that faces an exterior of the vehicle 12. In examples that use the second substantially transparent substrate 38, the second substantially transparent substrate 38 is spaced from the first substantially transparent substrate 36 by a predetermined distance and includes a third surface 44 and a fourth surface 46. The third surface 44 faces the second surface 42 (i.e., the interior cabin of the vehicle 12), and the fourth surface 46 faces the exterior of the vehicle 12. The antenna array 16 may generally be disposed on or formed with the first substantially transparent substrate 36. In some examples, a third substrate and/or laminate may be positioned between the antenna array 16 and the interior cabin to provide a smooth surface of the window 18 for an observer within the interior cabin. In other examples, the antenna array 16 is disposed on the third or fourth surface 44, 46 of the second substantially transparent substrate 38. It should be appreciated, however, that the conductive coating 20 (e.g., the antenna array 16) may alternatively be located on either the third or fourth surface 44, 46 of the second substantially transparent substrate 38. In some embodiments, the antenna array 16 may include a ground plane conductor spaced from a plurality of antennas 48 by a dielectric layer.

The antenna array 16 includes the plurality of antennas 48 formed in or on the window 18 via the conductive coating 20. For example, the conductive coating 20 may be at least partially (e.g., partially or fully) disposed in recesses 49 formed in the first substantially transparent substrate 36 (FIG. 4A) or may be disposed on (e.g., directly) and project from the second surface 42 without the recesses 49 in the first substantially transparent substrate 36. When the plurality of antennas 48 is exposed to a radio frequency signal, the plurality of antennas 48 may communicate that radio frequency signal along the conductive coating 20 to the controller 22. Similarly, the controller 22 may be configured to communicate an electrical signal to the plurality of antennas 48 so that the plurality of antennas 48 produces the radio frequency signals directed generally toward the interior cabin of the vehicle 12. The conductive coating 20 may be a substantially transparent conductive oxide ("TCO"), such as Indium Tin Oxide ("ITO") and/or other materials that are both substantially transparent and electrically conductive.

Figure 3:
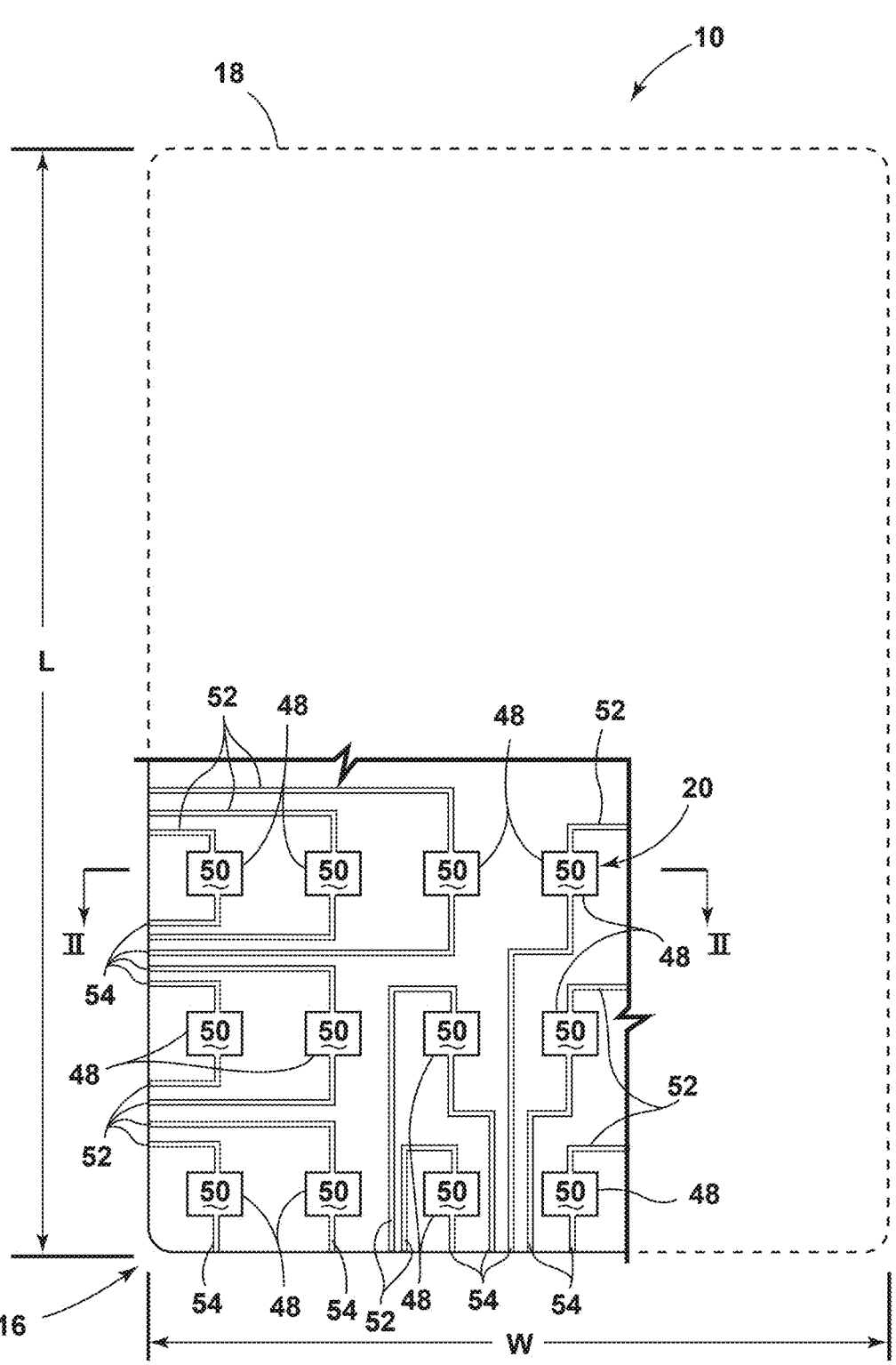
FIG. 3 is a bottom plan view of a sensing apparatus according to one aspect of the present disclosure.

The conductive coating 20 may be substantially transparent in a visible light spectral range of between about 380 nm and about 700 nm. In some embodiments, at least one (e.g., one, some, or all) of the plurality of antennas 48 is a patch antenna 50, as shown in FIG. 3. However, in some embodiments, it should be appreciated that the conductive coating 20 may form a portion of any other type of antenna such as a strip line antenna, a dipole antenna, a monopole antenna, a fractal antenna, etc., without departing from the scope of the disclosure.

Referring now to FIG. 3, the antenna array 16 is illustrated as an array of patch antennas 50 incorporated within one of the sunroof windows 32, 34. The conductive coating 20 includes the antenna array 16 and at least one electrical conductor 52, 54. Each patch antenna 50 may be individually controlled by the controller 22 with high-frequency signals communicated via the at least one electrical conductor 52, 54. For example, the at least one electrical conductor 52, 54 may include a first electrical conductor 52 and/or a second electrical conductor 54 each electrically coupling one or more of the patch antennas 50 with the controller 22. In some embodiments, the at least one electrical conductor 52, 54 is a single electrical conductor for each patch antenna 50 and the second electrical conductor 54 is omitted. In the example illustrated, either or both of the first and/or second electrical conductors 52, 54 can be energized by electrical signals from the controller 22 to cause the patch antenna 50 to emit a wireless radio frequency signal toward the interior cabin of the vehicle 12. As will be further described in reference to FIG. 4B, the at least one electrical conductor 52, 54 may also be employed to carry a power signal (e.g., an electrical current). In some examples, the conductive coating 20, or tracing, in the window 18 forms individually controlled groups of the plurality of antennas 48 (e.g., the patch antennas 50). For example, groups including two or more of the plurality of antennas 48 may be electrically coupled with one another to form one or more individually controlled regions of the antenna array 16. In this example, the at least one electrical conductor 52, 54 corresponds to several patch antennas 50 with multiple first antennas branching off from the at least one electrical conductor 52, 54. As further described herein with respect to FIG. 5, the degree of individualized control over the plurality of antennas 48 may correspond to a level of control over the phase angle Θ.

It is generally contemplated that each of the plurality of antennas 48 (e.g., the patch antennas 50) of the antenna array 16 has an area in a range of about 1 cm$^2$ to about 5 cm$^2$; however, this size can vary outside of these parameters depending on the desired operational parameters. In some embodiments, the area is about 1 cm$^2$ or about 3 cm$^2$ with expected nominal variations as a result of manufacturing and/or operational limitations and tolerances. Each (or select) of the antennas 48 may be square-shaped or rectangular-shaped. In other arrangements, each or select of the antennas 48 may be shaped with one or more arcuate perimeters (e.g., a circular-shape or an oval-shape). In still other arrangements, each or select of the antennas 48 may have a polygonal shape other than a square or rectangular. An angular accuracy of the antenna array 16 corresponds to the wavelength of the signal transmitted/received, the size of the antenna array 16, and the relative spacing between each of the antennas 48. In particular, the angular accuracy is determined by the speed of light divided by the frequency divided by the dimension, or length L, of the antenna array 16. In general, the antenna array 16 may be operable between about 27 GHz to at least about 80 GHz. In some embodiments, the antenna array 16 may be operable between two RADAR frequency bands utilized in automotive applications, such as about 30 GHz and about 60 GHz. For example, an antenna array 16 having a length L of 1 m may result in an angular accuracy of between about 0.5° (at 30 GHz) and about 0.250 (at 60 GHz). According to some aspects of the disclosure, the angular accuracy of the antenna array 16 may be an aggregate of the angular accuracies provided by each of the plurality of antennas 48. In some embodiments, an antenna array 16 that has a length L of about 50 cm may have an angular accuracy, of about 1.1° at about a 30 GHz frequency. It is contemplated from the disclosure that the size of the antenna array 16 may directly correlate to an area of the window 18. For example, the window 18 may have an area between about 0.96 m² (e.g., 1.2 m by 8 m) and about 1.8 m² (e.g., 1.5 m by 1.2 m) and the antenna array 16 may cover an area between about 0.9 m² and about 1.9 m². In other words, the antenna array 16 may include an outer perimeter that covers an area of between about 80% and about 99% of the area of an outer perimeter of the window 18, for example, between about 90% and about 97%, between about 92% and about 95%, or about 94%. The dimensions (e.g., length L and/or width W) of the antenna array 16 may allow for an angular accuracy of less than 1°.

Referring now to FIG. 4A, the antenna array 16 is illustrated incorporated adjacent to an electro-optic element 58 of the window 18. The electro-optic element 58 includes a first electrode 60 and a second electrode 62, each being substantially transparent. For example, the first and second electrodes 60, 62 may be formed of a TCO material, such as ITO. The first electrode 60 is disposed on the second surface 42. The second electrode 62 is disposed on the third surface 44. The first electrode 60 is spaced from the second electrode 62 to define a chamber 64 therebetween to receive an electro-optic medium 66, which may be an electrochromic fluid. The electro-optic medium 66 may be switchable between a substantially clear or transmissive state and a substantially darkened or non-transmissive state. The chamber 64 is sealed by seals (not pictured) that extend between the first and second electrodes 60, 62 and/or the first and second substantially transparent substrates 36, 38. When electrical power is applied to the electro-optic element 58 (e.g., a voltage drop between the first electrode 60 and the second electrode 62), electrical current flows through the electro-optic medium 66 to cause the electro-optic element 58 to be in the darkened state.

The first electrode 60 may serve as a negative/neutral electrode of the electro-optic element 58. In some optional examples, the first electrode 60 of the electro-optic element 58 may also serve as a ground plane conductor for the antenna array 16. In some embodiments, the antenna array 16 may include the ground plane conductor other than the first electrode 60 and the ground plane conductor may be spaced from the plurality of antennas 48 by a dielectric layer. The ground plane conductor may provide for an increased gain of the antenna array 16 and/or for shielding the antenna array 16 from interference with other radio-frequency signals. The first substantially transparent substrate 36, which may be an insulator such as glass, may operate as the dielectric layer between the ground plane conductor and the plurality of antennas 48 to electrically insulate the plurality of antennas 48 from the ground plane conductor. When the first electrode 60 is incorporated as a ground plane conductor, the conductive coating 20 can have a narrower cross-section and require less conductive material than incorporation of an antenna array 16 separate from the electro-optic element 58 within the window 18. It is contemplated that the ground plane conductor and/or the dielectric layer, or the respective functions of these elements, may be omitted in various implementations of the sensing apparatus 10.

Referring to FIG. 4B, another configuration of the electro-optic element 58 incorporated with the antenna array 16 is illustrated. In this configuration, the antennas 48 and/or the at least one electrical conductors 52, 54 serve as the first electrode 60 for the electro-optic element 58. Although each of the at least one electrical conductor 52, 54 is isolated from one another for purposes of transmission of high-frequency signals, the at least one electrical conductor 52, 54 may be subject to a common voltage or grounding. The capability of one or more of the at least one electrical conductor 52, 54 to transmit two signals simultaneously (e.g., a power signal and a high-frequency signal) relates to the electrical characteristics of the signals applied to the electro-optic element 58 and the antenna array 16. Because the antenna array 16 is operable with high-frequency alternating signals, operation of the antenna array 16 does not interfere with the electro-optic operation of the electro-optic element 58. In these examples, the electro-optic element 58 is operable with direct current (DC) voltage, which is not affected by the high-frequency signals (e.g., analog signals) of the antenna array 16.

With reference to FIG. 5, the antenna array 16 is operable to transmit and/or receive radio frequency signals within a phase beam 67 operable at a phase angle Θ determined by the controller 22. The phase angle Θ is the angle of the phase beam 67 relative to a plane 69 in which the antenna array 16 extends (e.g., along the length L and width W). More specifically, the phase angle Θ is a smallest angle between the phase beam 67 and the plane 69. The phase beam 67 is controlled via a phase shift controller 68 (see FIG. 6) acting as a steering mechanism to steer the phase beam 67 in a particular direction by controlling the time at which each of the plurality of antennas 48 emits a particular frequency. By time-shifting/time-delaying the signal transmitted from the plurality of antennas 48, the individual radio frequency waves transmitted are superimposed along the phase beam 67.

The angular accuracy of the phase beam 67, represented by bounds 70, allows the phase beam 67 to operate within a tolerance. Although the bounds 70 illustrated are represented along a vehicle-width direction, it is contemplated that similar bounds 70 may extend in the frontward and rearward directions resulting in the phase beam 67 being defined by a three-dimensional shape of the bounds 70. For example, the phase beam 67 may operate within a conical shape. A depth resolution of the phase beam 67 may decrease as the phase beam 67 travels from the antenna array 16. For example, identification of a state of a first object positioned closer to the antenna array 16 (e.g., a headrest of a vehicle seat) than a second object (e.g., a floor of the vehicle 12) may be more accurate than identification of a state of the second object. It is generally contemplated that the phase beam 67 may have a phase angle range 71 that matches or exceeds the interior cabin of the vehicle 12, as illustrated by the dashed lines in FIG. 5. Therefore, the controller 22 is operable to communicate an instruction to the phase shift controller 68 to limit the phase angle range 71 to an operating range 72 that is within the interior cabin of the vehicle 12. In this way, the signals may be transmitted/received from the vehicle 12 and not neighboring vehicles.

Referring now to FIG. 6, the wireless sensing circuit 14 is illustrated in communication with a vehicle control module 74 via a communication bus 76. For example, the controller 22 is configured to deliver signals to the vehicle control module 74 via the communication bus 76. The controller 22 is configured to communicate location/occupant information, such as presence, location, and vital signs (such as a breathing rate) of the occupant that is determined based on control of the antenna array 16. The controller 22 includes a processor 78 that has one or more circuits configured to receive signals from the communication bus 76 and control the sensing apparatus 10. The processor 78 is in communication with a memory 80 configured to store instructions to control operations of the sensing apparatus 10. For example, the memory 80 may be configured to store one or more scanning patterns from the sensing apparatus 10 and the controller 22 (e.g., the processor 78) may be configured to identify the presence, location, and/or vital signs of an occupant in the interior cabin of the vehicle 12. The controller 22 is also in communication with the phase shift controller 68 to control the phase beam 67. The controller 22 also controls the antenna array 16 with different frequencies to adjust the phase angle Θ and/or increase angular accuracy. Further, the controller 22 may be in communication with one or more of the electro-optic element 58 of the window 18. For example, the controller 22 may be configured to control a voltage output of a power supply (not shown) that controls darkening or clearing of the window 18.

In operation, the controller 22 is configured to employ the antenna array 16 to scan the interior cabin of the vehicle 12 to determine the presence of an occupant within the interior cabin. The controller 22 may also determine, based on information received from the antenna array 16, whether an occupant in the interior cabin is a child. For example, because the phase beam 67 operates with a narrow angular accuracy (e.g., less than 1 degree), shapes and sizes of objects and occupants in the vehicle 12 are identified from the radio frequency feedback. Continuing with this operation, the controller 22 may also communicate with the vehicle control module 74 to identify that a driver has left the vehicle 12, and that a child remains inside the interior cabin of the vehicle 12. The controller 22 is configured to communicate an instruction to the vehicle control module 74 to alert the driver of the vehicle 12, via an audible warning, light indicator, text message, graphic generation, or the like, that the child has been left in the vehicle 12. Alternatively, the antenna array 16 may be employed to detect vital information such as blood flow in arteries (e.g., the presence of a heart rate), whether the occupant, such as the child, is breathing, and/or a breathing rate of an occupant. By way of example, the controller 22 may employ a time-of-flight analysis to signals transmitted and received via the antenna array 16 to measure distance from the antenna array 16 to an object. The controller 22 is alternatively, or additionally, configured to employ frequency Doppler shift analysis to determine relative velocities, such as velocity of blood, moving parts of a heart, or other moving parts of the occupant.

The above example is non-limiting. The controller 22 may operate with the antenna array 16 and the phase shift controller 68 to determine many cabin-sensing events not discussed in detail, such as detection of the number of occupants in the vehicle 12, identification of the occupants via scanning of facial features, etc.

In general, the present disclosure relates to an antenna array 16, or system, with a considerable resolution. The antenna system may be incorporated into a portion of a vehicle roof 24, such as a sunroof window 32, 34. To maintain the functionality of the sunroof window 32, 34, the antenna array 16 may be substantially transparent. In this way, the sunroof window 32, 34 may provide sunlight to the interior cabin, as well as provide for wireless RADAR detection of objects/occupants in the vehicle 12. One or more components of the sensing apparatus 10 (e.g., antenna array 16) may be incorporated into the entire inside or outside surface of the sunroof window 32, 34. Such a large area may allow the antenna array 16 to have a vast range of detection and transmission of radio frequency waves employed for RADAR detection. The antenna array 16 may be controlled to generate and direct the phase angle Θ. The large size (i.e., area of coverage) of the antenna array 16 may allow the antenna system to focus, with a high degree of resolution, on a specific region within the vehicle 12. This may allow the antenna system to detect a precise location of an occupant, identifying features of an occupant, vital signs of the occupant, other activities of the occupant, and/or the like.

The conductive coating 20 (e.g., the antenna array 16 and the at least one electrical conductor 52, 54) may further be incorporated with an electro-optic element 58 in the window 18. By providing the conductive coating 20 with the electro-optic element 58, two functions may be served simultaneously: RADAR sensing, and dimming control. In addition, electrically integrating the antenna system into the electro-optic element 58 can reduce the amount of conductive material needed in the window 18 to provide both sensing and dimming functions.

According to one aspect of the present disclosure, a sensing apparatus for a vehicle includes a window, a wireless sensing circuit, and a controller. The wireless sensing circuit includes a conductive coating coupled to the window. The conductive coating includes an antenna array that is configured to communicate a radio frequency at a phase angle. Further, a controller is in communication with the antenna array and configured to communicate a first signal to the antenna array to control the phase angle.

According to another aspect, the window is configured as a sunroof.

According to another aspect, the antenna array is substantially transparent in a visible light spectral range.

According to another aspect, the window includes an electro-optic element and the antenna array is disposed adjacent to the electro-optic element.

According to another aspect, the electro-optic element includes at least one electrode at least partially formed by the antenna array.

According to another aspect, the antenna array is configured to conduct an electrical current across an electro-optic medium of the electro-optic element.

According to another aspect, the electro-optic element is configured to selectively dim the window.

According to another aspect, the window includes a substrate having a first surface and a second surface, opposite the first surface, and wherein the antenna array is disposed adjacent to the first surface and at least one electrode of the electro-optic element is disposed adjacent to the second surface.

According to another aspect, the antenna array is configured to operate with a first electrical frequency, and wherein the at least one electrode is configured to operate with a second electrical frequency different than the first electrical frequency.

According to another aspect, the phase angle has an angular accuracy of less than 1 degree.

According to another aspect, the controller is further configured to determine a phase angle range corresponding to a region of an interior cabin of the vehicle, modify the phase angle to the region of the interior cabin, and control the antenna array based on the phase angle range.

According to another aspect, the controller is further configured to receive a second signal from the antenna array, and determine, based on the second signal, a presence of an occupant of said vehicle.

According to another aspect, the controller is further configured to receive a second signal from the antenna array, and determine, based on the second signal, a vital sign of an occupant of said vehicle.

According to another aspect of the present disclosure, a window for a vehicle includes a first substrate including a first surface and a second surface, a second substrate including a third surface and a fourth surface, a first electrode disposed on the third surface, an electro-optic medium disposed between the first electrode and the second surface, and a plurality of patch antennas disposed adjacent to the second surface. Further, the plurality of patch antennas is substantially transparent in a visible light spectral range.

According to another aspect, the plurality of patch antennas are in contact with the electro-optic medium and configured to conduct an electrical current across the electro-optic medium.

According to another aspect, the first electrode is configured as a ground plane conductor for the plurality of patch antennas.

According to yet another aspect of the present disclosure, a sensing apparatus for a vehicle includes a window, a wireless sensing circuit, and a controller. The wireless sensing circuit includes a conductive coating coupled to the window. The conductive coating includes a plurality of antennas and more than one electrical conductor. Each electrical conductor is in contact with some but not all of the plurality of antennas. Further, a controller is in communication with the more than one electrical conductor and configured to communicate a first signal to some of the plurality of antennas to provide a first phase angle and a second signal to some of the plurality of antennas to provide a second phase angle.

According to another aspect, the first phase angle is directed towards a first region on an interior cabin in the vehicle and the second phase angle is directed to a second region on the interior cabin.

According to another aspect, the first phase angle is different than the second phase angle.

According to another aspect, the conductive coating is substantially transparent in a visible light spectral range.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures, members, connectors, and/or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents.

What is claimed is:

1. A sensing apparatus for a vehicle, the sensing apparatus comprising:
   a window including an outer perimeter and an electro-optic element, the electro-optic element including:
      a first substrate including a first surface configured to face an interior of the vehicle and a second surface configured to face an exterior of the vehicle;
      a second substrate including a third surface and a fourth surface;
      a first electrode disposed on the third surface; and
      an electro-optic medium disposed between the first electrode and the second surface;
   a wireless sensing circuit includes a conductive coating coupled to the window and disposed adjacent to and across a perimeter of the first or second surface of the first substrate;
   the conductive coating includes an antenna array that is configured to communicate a radio frequency at a phase angle, the antenna array covering an area between 80% and 99% of the area defined by the outer perimeter; and
   a controller in communication with the antenna array and configured to communicate a first signal to the antenna array to control the phase angle.

2. The sensing apparatus of claim 1, wherein the window is configured as a sunroof.

3. The sensing apparatus of claim 1, wherein the antenna array is transparent in a visible light spectral range.

4. The sensing apparatus of claim 1, wherein the electro-optic element includes a second electrode at least partially formed by the antenna array.

5. The sensing apparatus of claim 4, wherein the antenna array is configured to conduct an electrical current across an electro-optic medium of the electro-optic element.

6. The sensing apparatus of claim 5, wherein the electro-optic element is configured to selectively dim the window.

7. The sensing apparatus of claim 1, wherein the antenna array is disposed adjacent to the first surface and a second electrode of the electro-optic element is disposed adjacent to the second surface.

8. The sensing apparatus of claim 7, wherein the antenna array is configured to operate with a first electrical frequency, and wherein the second electrode is configured to operate with a second electrical frequency different than the first electrical frequency.

9. The sensing apparatus of claim 1, wherein the phase angle has an angular accuracy of less than 1 degree.

10. The sensing apparatus of claim 1, wherein the controller is further configured to:

determine a phase angle range corresponding to a region of an interior cabin of the vehicle;

modify the phase angle to the region of the interior cabin; and control the antenna array based on the phase angle range.

11. The sensing apparatus of claim 1, wherein the controller is further configured to:

receive a second signal from the antenna array; and determine, based on the second signal, a presence of an occupant of said vehicle.

12. The sensing apparatus of claim 1, wherein the controller is further configured to:

receive a second signal from the antenna array; and determine, based on the second signal, a vital sign of an occupant of said vehicle.

13. A window for a vehicle comprising:

a first substrate including a first surface configured to face an interior of the vehicle and a second surface configured to face an exterior of the vehicle;

a second substrate including a third surface and a fourth surface;

a first electrode disposed on the third surface;

an electro-optic medium disposed between the first electrode and the second surface; and a plurality of patch antennas disposed adjacent to and across a perimeter of the second surface, wherein the plurality of patch antennas are transparent in a visible light spectral range.

14. The window of claim 13, wherein the plurality of patch antennas are in contact with the electro-optic medium and configured to conduct an electrical current across the electro-optic medium.

15. The window of claim 13, wherein the first electrode is configured as a ground plane conductor for the plurality of patch antennas.

16. A sensing apparatus for a vehicle, the sensing apparatus comprising:

a window including an electro-optic element, the electro-optic element including:

a first substrate including a first surface configured to face an interior of the vehicle and a second surface configured to face an exterior of the vehicle;

a second substrate including a third surface and a fourth surface;

a first electrode disposed on the third surface; and an electro-optic medium disposed between the first electrode and the second surface;

a wireless sensing circuit includes a conductive coating coupled to the window and disposed adjacent to and across a perimeter of the first or second surface of the first substrate;

the conductive coating includes an antenna array operable between two RADAR frequency bands between 27 GHz and 80 GHz, the antenna array includes a plurality of antennas and more than one electrical conductor, each electrical conductor in contact with some but not all of the plurality of antennas; and a controller in communication with the more than one electrical conductor and configured to communicate a first signal to some of the plurality of antennas to provide a first phase angle and a second signal to some of the plurality of antennas to provide a second phase angle.

17. The sensing apparatus of claim 16, wherein the first phase angle is directed towards a first region on an interior cabin in the vehicle and the second phase angle is directed to a second region on the interior cabin.

18. The sensing apparatus of claim 16, wherein the first phase angle is different than the second phase angle.

19. The sensing apparatus of claim 16, wherein the antenna array covers an area between 0.9 $m^2$ and 1.9 $m^2$.

* * * * *